(12) United States Patent
Suzuki et al.

(10) Patent No.: US 9,861,267 B2
(45) Date of Patent: Jan. 9, 2018

(54) VIDEO PROCESSOR FOR ENDOSCOPE, AND ENDOSCOPE SYSTEM INCLUDING THE SAME

(71) Applicant: OLYMPUS CORPORATION, Hachioji-shi, Tokyo (JP)

(72) Inventors: Tatsuhiko Suzuki, Hino (JP); Tomoki Iwasaki, Fuchu (JP); Susumu Hashimoto, Hachioji (JP); Toshihiro Hamada, Fuchu (JP); Yuji Kutsuma, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/240,254

(22) Filed: Aug. 18, 2016

(65) Prior Publication Data
US 2016/0353981 A1    Dec. 8, 2016

Related U.S. Application Data

(63) Continuation of application No. PCT/JP2015/070710, filed on Jul. 21, 2015.

(30) Foreign Application Priority Data

Jul. 29, 2014  (JP) .................................. 2014-154296

(51) Int. Cl.
*A61B 1/04*   (2006.01)
*G02B 23/26*  (2006.01)
(Continued)

(52) U.S. Cl.
CPC .............. *A61B 1/04* (2013.01); *A61B 1/0002* (2013.01); *A61B 1/0005* (2013.01);
(Continued)

(58) Field of Classification Search
CPC ... A61B 1/00006; A61B 1/00009; A61B 1/04; A61B 1/0002; A61B 1/0005;
(Continued)

(56) References Cited

U.S. PATENT DOCUMENTS

2002/0093518 A1* 7/2002 Nakano .................... H04N 5/14
                                                          345/643
2004/0143157 A1* 7/2004 Doguchi ............ A61B 1/00059
                                                          600/109
(Continued)

FOREIGN PATENT DOCUMENTS

CN       2303580 Y    1/1999
JP   2006-280541 A   10/2006
(Continued)

OTHER PUBLICATIONS

Feb. 9, 2017 Transmittal of Translation of International Preliminary Report on Patentability issued in International Patent Application No. PCT/JP2015/070710.
(Continued)

*Primary Examiner* — John P Leubecker
(74) *Attorney, Agent, or Firm* — Oliff PLC

(57) ABSTRACT

A video processor for an endoscope includes an image memory, an image processing unit, a display control unit and a recording unit. The image memory stores, as a sample image, an endoscope image which a user previously acquired. The image processing unit performs the image processing for changing an image quality of the sample image in accordance with a selection value selected by a user and produces a processed image. The display control unit causes a display unit to display the processed image. The recording unit records, as a setting value, a value relating to the selection value determined by the user. The image (Continued)

processing unit performs the image processing, based on the setting value, for the endoscope image.

8 Claims, 5 Drawing Sheets

(51) Int. Cl.
    *A61B 1/00*     (2006.01)
    *G02B 23/24*     (2006.01)
    *H04N 5/225*     (2006.01)
    *H04N 5/232*     (2006.01)

(52) U.S. Cl.
    CPC ...... *A61B 1/00006* (2013.01); *A61B 1/00009* (2013.01); *G02B 23/2484* (2013.01); *G02B 23/26* (2013.01); *H04N 5/2256* (2013.01); *H04N 5/23293* (2013.01); *H04N 2005/2255* (2013.01)

(58) Field of Classification Search
    CPC .............. A61B 1/00045; A61B 5/7435; H04N 5/23232; H04N 2005/2255; G06T 1/00; G06T 5/00
    See application file for complete search history.

(56) References Cited

U.S. PATENT DOCUMENTS

| | | | | |
|---|---|---|---|---|
| 2005/0020879 A1* | 1/2005 | Suzuki | ............... | A61B 1/00039 600/118 |
| 2005/0152667 A1* | 7/2005 | Park | ............... | G11B 19/025 386/243 |
| 2005/0212814 A1* | 9/2005 | Kubo | ............... | H04N 1/6013 345/614 |
| 2006/0241418 A1* | 10/2006 | Abe | ............... | A61B 1/00009 600/433 |
| 2006/0282867 A1* | 12/2006 | Mizuhashi | ............. | H04N 17/04 725/105 |
| 2008/0088710 A1* | 4/2008 | Iwamoto | ............ | H04N 1/32128 348/220.1 |
| 2009/0027732 A1* | 1/2009 | Imai | ............ | G06T 5/00 358/3.27 |
| 2009/0096933 A1* | 4/2009 | Iijima | ............ | H04N 5/445 348/700 |
| 2009/0207242 A1* | 8/2009 | Iwasaki | ............ | G02B 23/2484 348/68 |
| 2009/0303316 A1* | 12/2009 | Iwasaki | ............ | A61B 1/00022 348/65 |
| 2012/0038656 A1* | 2/2012 | Kang | ............ | G06T 1/00 345/581 |
| 2012/0201433 A1* | 8/2012 | Iwasaki | ............ | A61B 1/00009 382/128 |
| 2013/0314549 A1* | 11/2013 | Higuchi | ............ | H04N 17/04 348/175 |
| 2015/0002904 A1* | 1/2015 | Nakamura | ............ | G06K 15/1872 358/3.01 |
| 2015/0098646 A1* | 4/2015 | Paris | ............ | G06T 5/00 382/159 |
| 2015/0248197 A1* | 9/2015 | Peters | ............ | A61B 6/463 715/838 |
| 2016/0209995 A1* | 7/2016 | Jeon | ............ | G06T 5/003 |
| 2016/0269611 A1* | 9/2016 | Kutsuma | ............ | H04N 5/2351 |
| 2016/0309093 A1* | 10/2016 | Ishii | ............ | H04N 5/77 |
| 2016/0344975 A1* | 11/2016 | Hendrik | ............ | H04N 7/147 |

FOREIGN PATENT DOCUMENTS

| | | |
|---|---|---|
| JP | 2012-070993 A | 4/2012 |
| JP | 2012-249684 A | 12/2012 |

OTHER PUBLICATIONS

Oct. 27, 2015 International Search Report issued in Patent Application No. PCT/JP2015/070710.

Jun. 2, 2017 Office Aciton issued in Chinese Patent Application No. 201580003813.9.

\* cited by examiner

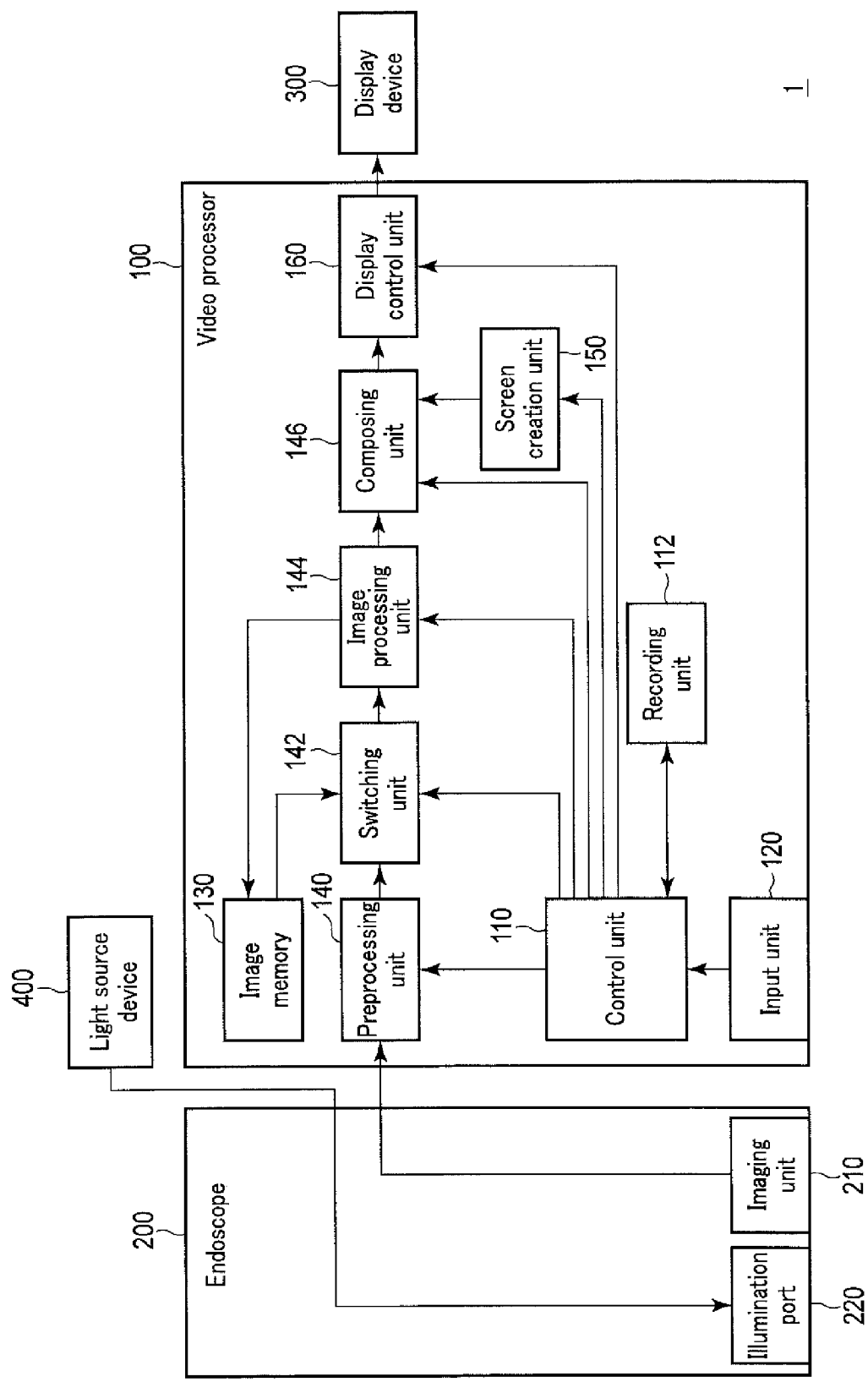
F I G. 1

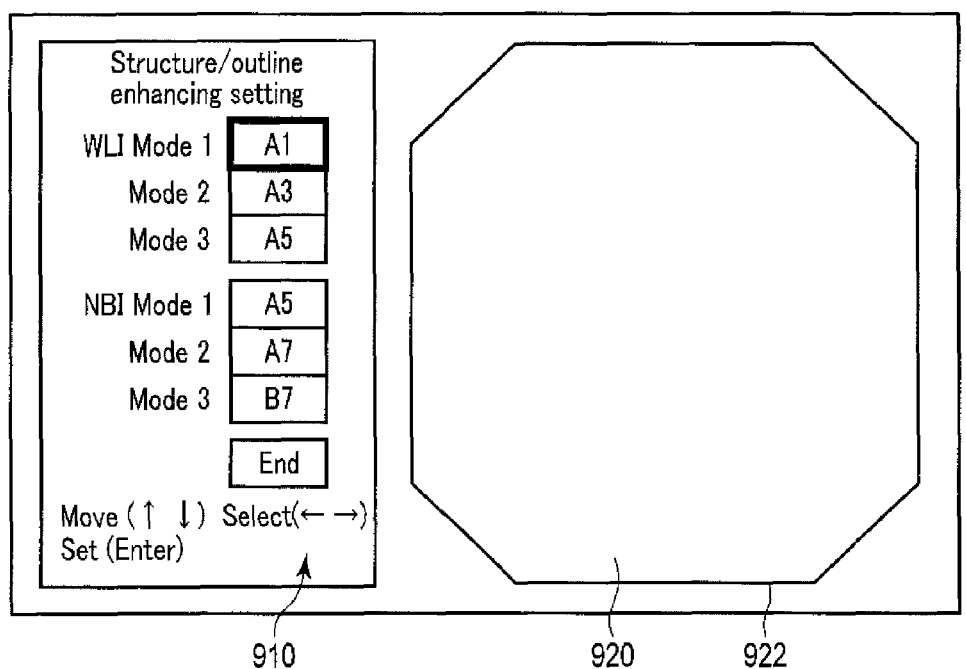
F I G. 2

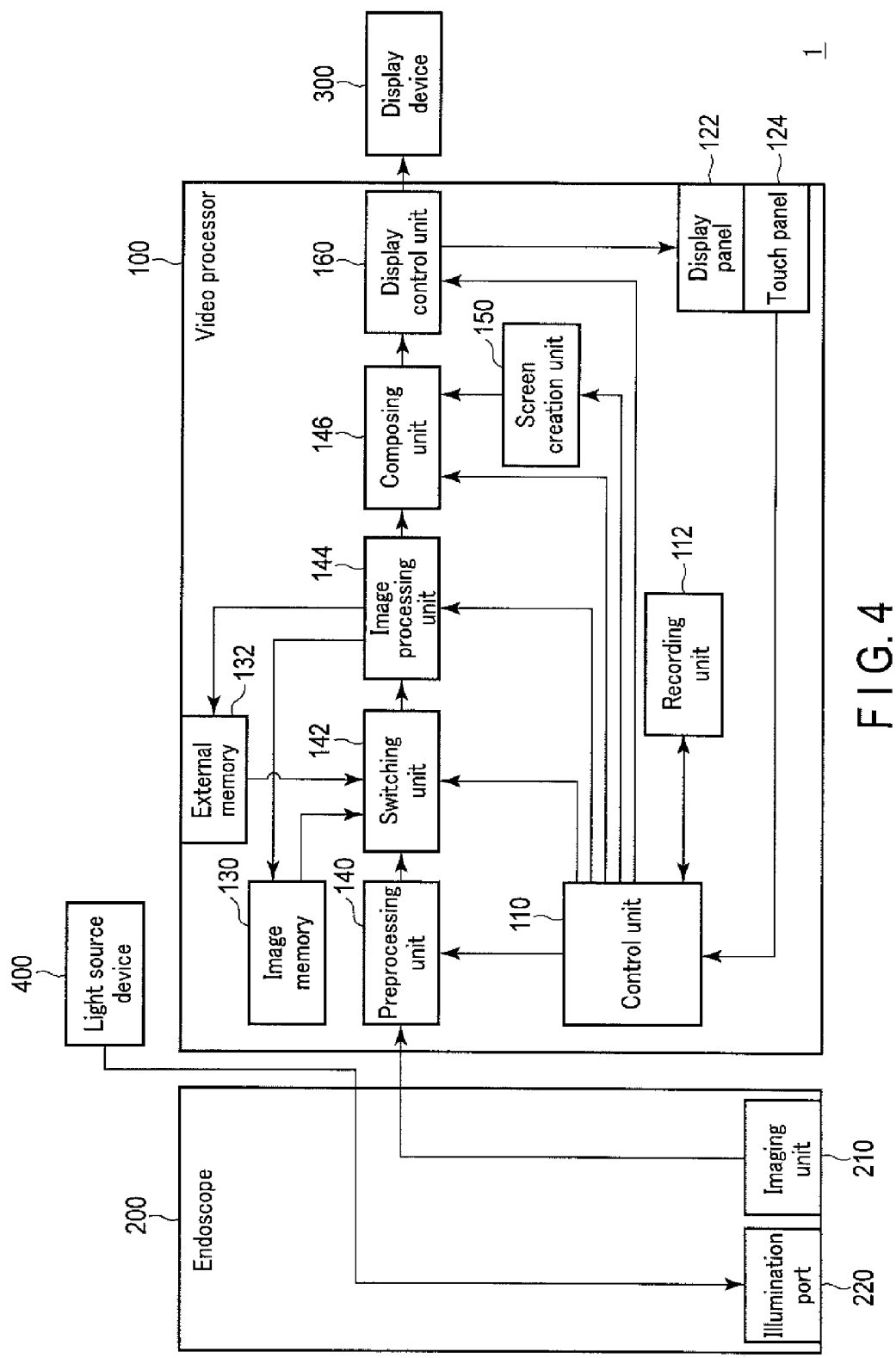
F I G. 4

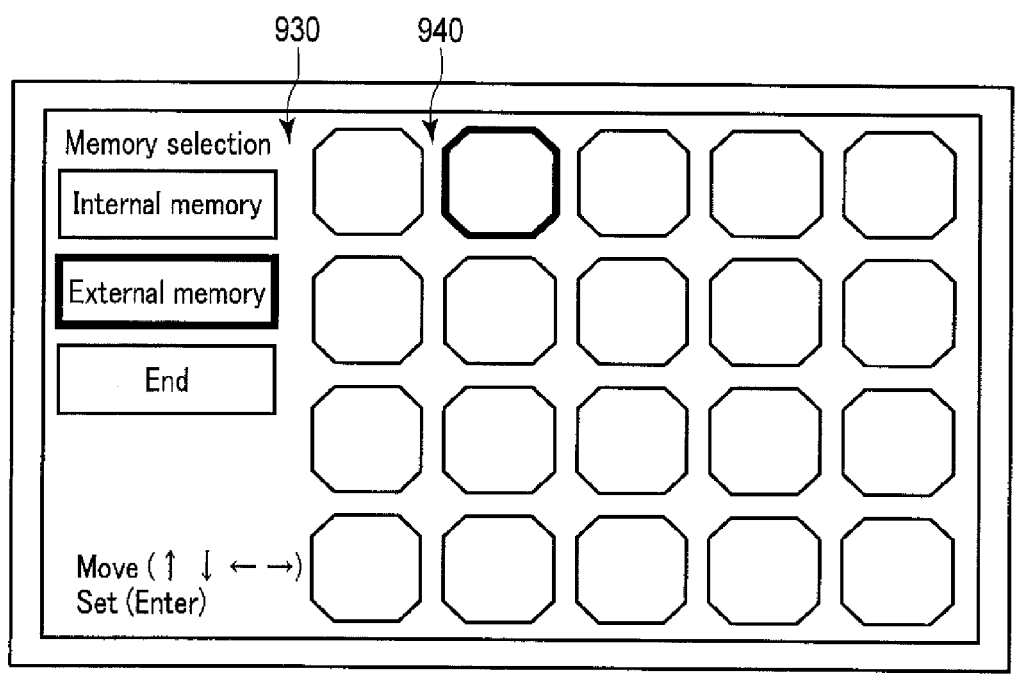
F I G. 5

VIDEO PROCESSOR FOR ENDOSCOPE, AND ENDOSCOPE SYSTEM INCLUDING THE SAME

CROSS-REFERENCE TO RELATED APPLICATIONS

This application is a Continuation Application of PCT Application No. PCT/JP2015/070710, filed Jul. 21, 2015 and based upon and claiming the benefit of priority from prior Japanese Patent Application No. 2014-154296, filed Jul. 29, 2014, the entire contents of all of which are incorporated herein by reference.

BACKGROUND OF THE INVENTION

1. Field of the Invention

The present invention relates to a video processor for an endoscope, and an endoscope system including the same.

2. Description of the Related Art

In a medical electronic endoscope, an image quality of an endoscope image may be adjusted. For example, Jpn. Pat. Appln. KOKAI Publication No. 2006-280541 discloses a technique relating to an endoscope system comprising a processor device that performs image processing of an endoscope image acquired by an endoscope, and an endoscope monitor that displays an endoscope image processed by the processor device, and in addition, an adjusting processor apparatus that adjusts a parameter of the endoscope image and an adjustment monitor that displays an image for adjustment. In the endoscope system, since the adjustment monitor displays details of adjustment of the parameter, the endoscope monitor can display only the endoscope image. Therefore, the parameter can be adjusted by the adjustment monitor, while an endoscopic diagnosis is continued by the endoscope monitor without interruption.

As described above, in general, when the image quality of an endoscope image is adjusted, the user adjusts the image quality while checking the image acquired by the endoscope. At this time, it is necessary that the endoscope be connected to a video processor to take an appropriate image by the endoscope.

BRIEF SUMMARY OF THE INVENTION

According to an aspect of the invention, a video processor for an endoscope that performs image processing for an endoscope image acquired by an imaging unit of an endoscope includes an image memory that stores, as a sample image, an endoscope image which a user previously acquired by the endoscope for setting an image quality; an image processing unit that performs the image processing for changing an image quality of the sample image in accordance with a selection value selected by a user and produces a processed image; a display control unit that causes a display unit to display the processed image; and a recording unit that records, as a setting value, a value relating to the selection value determined by the user, wherein the image processing unit performs the image processing, based on the setting value, for the endoscope image acquired by the imaging unit.

According to an aspect of the invention, an endoscope system includes the video processor and the endoscope.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing an outline of a configuration example of an endoscope system according to a first embodiment.

FIG. 2 is a diagram showing an example of a composite screen according to the first embodiment.

FIG. 4 is a block diagram showing a configuration example of an endoscope system according to a second embodiment.

FIG. 5 is a diagram showing an example of an image displayed on a display panel according to the second embodiment.

DETAILED DESCRIPTION OF THE INVENTION

[First Embodiment]

Figure 3:
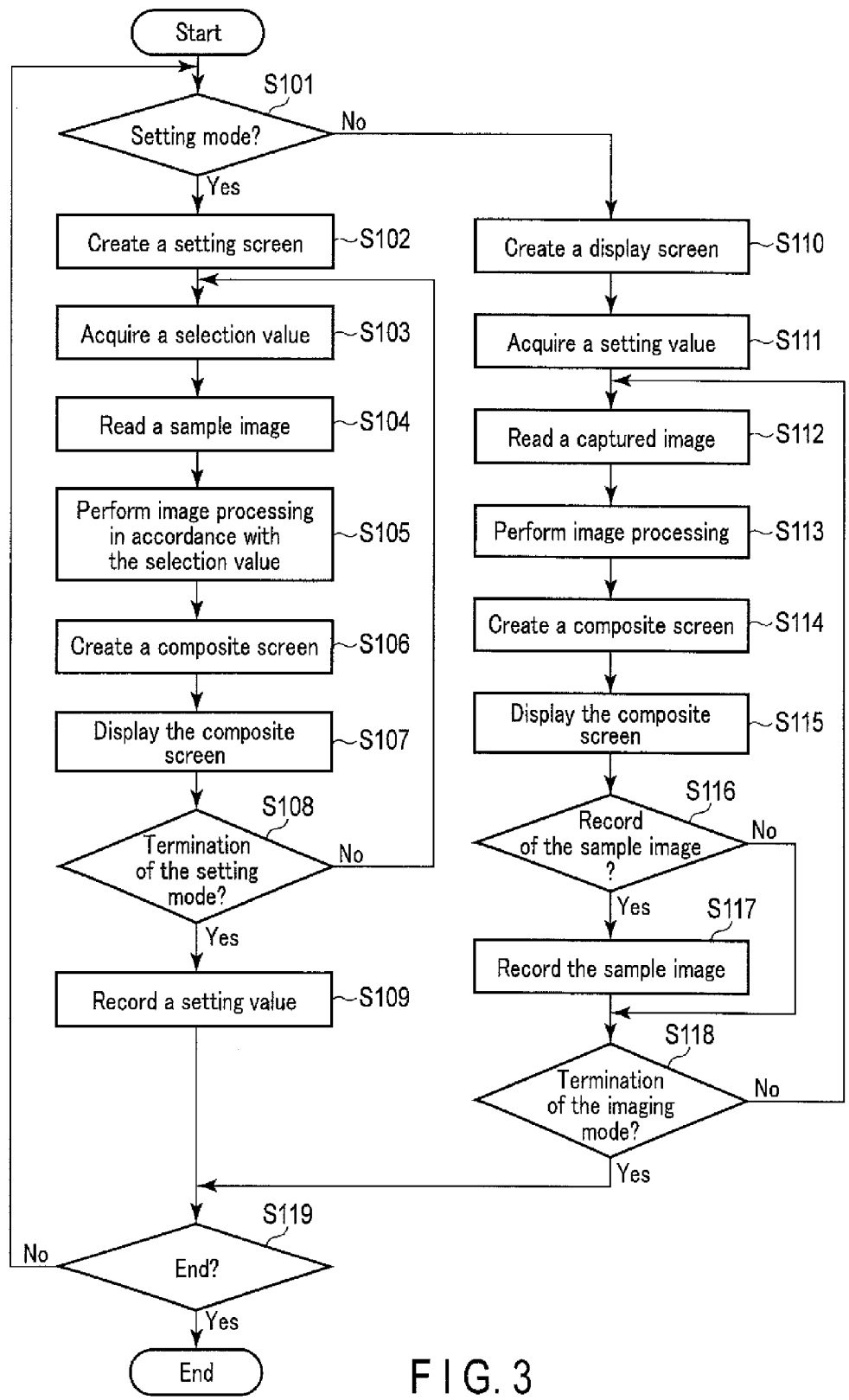
FIG. 3 is a flowchart showing an example of a process in a video processor according to the first embodiment.

The first embodiment of the present invention will be explained with reference to the drawings. FIG. 1 shows an outline of a configuration example of an endoscope system 1 according to the embodiment. As shown in FIG. 1, the endoscope system comprises a video processor 100 according to the embodiment, a medical endoscope 200, a display device 300 as a display unit, and a light source device 400.

The endoscope 200 is a general medical electronic endoscope. The endoscope 200 comprises an imaging unit 210. The imaging unit 210 includes an imaging element such as a CCD. Furthermore, the endoscope 200 comprises an illumination port 220, through which an illumination light for illuminating an object is emitted. The illumination port 220 is provided with, for example, a lens.

The display device 300 is a general display device. The display device 300 includes, for example, a liquid crystal display. The display device is not limited to a liquid crystal display but may be any type, such as a CRT display.

The light source device 400 includes a light source of an illumination light that is emitted through the illumination port 220. The light source device 400 and the illumination port 220 are connected via, for example, an optical fiber. The illumination light is guided via the optical fiber and emitted through the illumination port 220.

The video processor 100 acquires an endoscope image captured by the endoscope 200, provides image processing for the endoscope image, and causes the display device 300 to display the processed image. The image processing includes a process of enhancing a structure or outline of a blood vessel or the like included in the endoscope image.

The video processor 100 comprises a control unit 110, a recording unit 112, an input unit 120, an image memory 130, a preprocessing unit 140, a switching unit 142, an image processing unit 144, a composing unit 146, a screen creation unit 150, and a display control unit 160. The control unit 110, the preprocessing unit 140, the switching unit 142, the image processing unit 144, the composing unit 146, the screen creation unit 150, and the display control unit 160 are each formed of, for example, a central processing unit (CPU) or an application specific integrated circuit (ASIC). The recording unit 112 and the image memory 130 are each formed of, for example, a general semiconductor memory.

The control unit 110 controls operations of the respective units of the video processor 100. The recording unit 112 records programs, parameters, etc. necessary for operations of the control unit 110. The parameters recorded in the recording unit 112 include image processing parameters relating to image processing described later. The control unit 110 and the like operate in accordance with the programs recorded in the recording unit 112.

The input unit 120 includes a general input device, such as a switch, a button, and a keyboard. The input unit 120 receives an input by a user, and outputs the input to the control unit 110.

The image memory 130 stores as a sample image an endoscope image, which the user previously captured via the endoscope 200. The sample image stored in the image memory 130 may be acquired by, for example, the imaging unit 210, and recorded as so-called raw data that has not been processed, or recorded as data including processed data and details of the image processing that has been performed. An image quality can be adjusted by image processing of a sample image. The image memory 130 stores as sample images a plurality of images, which have been captured in different modes, such as a WLI mode and an NBI mode.

The screen creation unit 150 creates, under the control of the control unit 110, a screen derived from an image other than either of the images acquired by the imaging unit 210 of the endoscope 200 or the images recorded in the image memory 130, of the screens to be displayed in the image display device 300. The screen creation unit 150 creates, for example, a setting screen and a screen including information on the endoscope 200 and other information to assist the user. The screen creation unit 150 outputs the created screen to the composing unit 146.

The preprocessing unit 140 acquires an endoscope image captured by the imaging unit 210 of the endoscope 200 and performs preprocessing of the image under the control of the control unit 110. The preprocessing unit 140 outputs the preprocessed image to the switching unit 142.

The switching unit 142 selects, under the control of the control unit 110, one of an endoscope image captured by the imaging unit 210 and processed by the preprocessing unit 140 and a sample image recorded in the image memory 130 as an image to be subjected to the subsequent image processing. The switching unit 142 outputs the selected image to the image processing unit 144.

The image processing unit 144 performs image processing for an image acquired from the switching unit 142 under the control of the control unit 110. The image processing includes a change of a color tone, contrast and brightness, a change of intensity of noise reduction, etc. The image processing performed by the image processing unit 144 includes structure enhancing and outline enhancing. The structure enhancing and the outline enhancing include, for example, a type of image processing to increase the viewability of a thick blood vessel and a type of image processing to increase the viewability of a thin blood vessel. In the structure enhancing and the outline enhancing, for example, the blood vessel enhancing level can be adjusted in, for example, eight stages. The image processing unit 144 outputs the processed image to the composing unit 146.

The composing unit 146 creates, under the control of the control unit 110, a composite screen composed of the processed image acquired from the image processing unit 144 and, for example, a setting screen created by the screen creation unit 150. An example of the screen created by the composing unit 146 is shown in FIG. 2. The screen shown in FIG. 2 includes a setting menu 910 and an image 920 processed by the image processing unit 144 and displayed within a frame 922. The composing unit 146 outputs the created composite screen to the display control unit 160.

The display control unit 160 outputs, under the control of the control unit 110, the composite screen acquired from the composing unit 146 to the display device 300, and causes the display device 300 to display the composite screen.

An operation of the endoscope system 1 according to the embodiment will be explained with reference to the flowchart shown in FIG. 3, focusing on the video processor 100 in particular. When the user desires to set a level of the structure/outline enhancing, the user inputs to that effect in the video processor 100 through the input unit 120. At this time, the video processor 100 performs an operation of a setting mode. On the other hand, when the user desires not the setting mode, but a general operation of displaying an image acquired by the endoscope 200 in the display device 300, the user inputs to that effect in the video processor 100 through the input unit 120. At this time, the video processor 100 performs an operation of an imaging mode. In the imaging mode, image processing is performed with a setting value, such as a structure/outline enhancing level set in the setting mode.

In step S101, the control unit 110 determines whether the setting mode is selected or not. If it is determined that the setting mode is selected, the process proceeds to step S102.

In step S102, the control unit 110 causes the screen creation unit 150 to create a setting screen. The screen creation unit 150 is a screen including, for example, the setting menu 910 and the frame 922 that displays the image 920 processed by the image processing unit 144, as shown in FIG. 2.

Observations using the endoscope 200 include a white-light imaging mode (WLI mode) for illuminating an object with white light, and a narrow band imaging mode (NEI mode) for illuminating an object with narrow band light. The setting menu 910 created by the screen creation unit 150 shows three options of different types and levels of structure/outline enhancing in the WLI mode, and three options of different types and levels of structure/outline enhancing in the NBI mode.

In the example shown in FIG. 2, the WLI mode has three options of different levels of enhancing a blood vessel for A type image processing to increase the viewability of a thick blood vessel. Specifically, in FIG. 2, "A1" represents that the type is A and the enhancing level is 1.Similarly, "A3" represents that the type is A and the enhancing level is 3, and "A5" represents that the type is A and the enhancing level is 5.

In the example shown in FIG. 2, the NEI mode has two options of different levels of enhancing a blood vessel for A type image processing to increase the viewability of a thick blood vessel, and one option of a level of enhancing a blood vessel for B type image processing to increase the viewability of a thin blood vessel. Specifically, in FIG. 2, "A5" represents that the type is A and the enhancing level is 5, "A7" represents that the type is A and the enhancing level is 7, and "B7" represents that the type is B and the enhancing level is 7.

The user selects a structure/outline enhancing level in the WLI mode, or a structure/outline enhancing level in the NBI mode.

In step S103, the control unit 110 acquires an input by the user from the input unit 120, and acquires, as selection values, an observation mode selected by the user and the type and level of the structure/outline enhancing selected by the user.

In step S104, the control unit 110 causes the switching unit 142 to read a sample image from the image memory 130. If the WLI mode is selected by the user in step S103, an endoscope image acquired in the WLI mode is read as a sample image. On the other hand, if the NBI mode is selected by the user in step S103, an endoscope image acquired in the NBI mode is read as a sample image.

In step S105, the control unit 110 causes the image processing unit 144 to perform image processing in accordance with the structure/outline enhancing level etc. acquired in step S103. As a result of the image processing, a processed image, in which the image quality has been changed on the basis of a sample image, is produced.

The sample image is recorded as so-called raw data, which is unprocessed data, for example, acquired by the imaging unit 210. In this case, in the observation time when the sample image is acquired, the raw data is subjected to predetermined image processing and an image for observation is produced. On the other hand, the image processing performed for the raw data in step S105 may be different from the image processing performed in the observation time. Therefore, various processed images can be produced on the basis of the sample image.

Furthermore, the sample image may be recorded as data including the processed image data and the details of the image processing that has been performed. In this case, in the observation time when the sample image was acquired, the processed image was used as an image for observation. In step S105, the processed image is returned to an unprocessed image based on the details of the image processing that has been performed and included in the data of the sample image, and the unprocessed image can be subjected to image processing different from that performed in the observation time. Therefore, various processed images can be produced on the basis of the sample image.

In step S106, the control unit 110 causes the composing unit 146 to compose the processed image produced in step S105 within the frame 922 of the setting screen produced in step S102, thereby creating a composite screen.

In step S107, the control unit 110 causes the display control unit 160 to display the composite screen created in step S106 in the display device 300.

In step S108, the control unit 110 determines whether a termination of the setting mode is input, that is, whether the setting mode should be terminated or not. If it is determined that the setting mode should not be terminated, the process returns to step S103. At this time, reading of the structure/outline enhancing level selected by the user as a selection value, and updating and displaying the processed image that has been processed in accordance with the selection value are repeated. On the other hand, if it is determined that the setting mode should be terminated in step S108, the process proceeds to step S109.

In step S109, the control unit 110 records, as a setting value, an image processing parameter relating to image processing selected by the user in the recording unit 112. Then, the process proceeds to step S119.

If it is determined in step S101 that the setting mode is not selected, namely, that the imaging mode is selected, the process proceeds to step S110.

In step S110, the control unit 110 causes the screen creation unit 150 to create a display screen. The screen to be displayed here is a screen including, for example, a frame that displays an endoscope image captured by the endoscope 200, and characters, etc. representing information such as conditions for imaging.

In step S111, the control unit 110 acquires a setting value including an image processing parameter corresponding to the structure/outline enhancing level etc. recorded in the recording unit 112.

In step s112, the control unit 110 causes the switching unit 142 to read an endoscope image captured by the imaging unit 210 and processed by the preprocessing unit 140.

In step S113, the control unit 110 causes the image processing unit 144 to perform image processing using the image processing parameter read in step 111 for the endoscope image read in step S112.

In step S114, the control unit 110 causes the composing unit 146 to compose the processed endoscope image produced in step S113 within the frame of the display screen produced in step s110, thereby creating a composite screen.

In step s115, the control unit 110 causes the display control unit 160 to display the composite screen created in step S114 in the display device 300.

In step S116, the control unit 110 determines whether or not the endoscope image currently displayed in the display device 300 should be recorded as a sample image. For example, if the user inputs through the input unit 120 an intention to record the currently displayed image as a sample image, it is determined that the image should be recorded as a sample image. If it is determined that the image should not be recorded as a sample image, the process proceeds to step S118. On the other hand, if it is determined that the image should be recorded as a sample image, the process proceeds to step S117.

In step S117, the control unit 110 causes the image processing unit 144 to record the currently displayed endoscope image as a sample image in the image memory 130. At this time, so-called raw data, which is unprocessed data acquired by the imaging unit 210, and data including processed data and details of the image processing that has been performed, are recorded in the image memory 130. Then, the process proceeds to step S118.

In step S118, the control unit 110 determines whether a termination of the imaging mode is input, that is, whether the imaging mode should be terminated or not. If it is determined that the imaging mode should not be terminated, the process returns to step S112. At this time, reading of the endoscope image from the imaging unit 210, and displaying a composite image including the processed image that has been processed in accordance with the setting value for the endoscope image, are continuously repeated. If it is determined in step S118 that the imaging mode should be terminated, the process proceeds to step S119.

In step S119, the control unit 110 determines whether the operation of the video processor 100 should be terminated by, for example, turning off the power source. If it is determined that the operation should not be terminated, the process returns to step S101. On the other hand, if it is determined that the process should be terminated, the process is terminated.

As described above, in the video processor 100 of the embodiment, a type and a level of structure/outline enhancing are set in the setting mode, while an image based on a sample image is displayed in the display device 300. In general, the structure/outline enhancing level or the like is adjusted by using a real-time endoscope image acquired by the endoscope 200. In this case, it is necessary that the endoscope 200 be connected to the video processor 100. It is also necessary that the light source device be connected to the endoscope 200. Furthermore, it is necessary that the endoscope 200 has captured a suitable object. In contrast, in this embodiment, the structure/outline enhancing level or the like is adjusted by using a sample image recorded in the image memory 130. Therefore, under the circumstance where the endoscope 200 is not connected to the video processor 100, or the endoscope 200 has not acquired a suitable image to perform adjustment even if it is connected to the video processor, the user can suitably adjust the structure/outline enhancing level or the like while checking a processed image.

Furthermore, in this embodiment, the composite screen as shown in FIG. 2 simultaneously displays, side by side on one screen, the setting menu 910 and the processed sample image which reflects real-time image processing. Therefore, the user can easily configure a desired setting while checking a processed image.

The sample image is not limited to an image captured by the user, but may be an image prerecorded in the processor before shipment. However, the user can more easily adjust the structure/outline enhancing level or the like if the image captured by the user is used as a sample image as in the embodiment, because in that case the user can easily imagine the relationship between the object and a processed image of the object to be displayed

[Second Embodiment]

The second embodiment of the present invention is explained below. In the following, matters different from the first embodiment will be explained. The same symbols as used in the first embodiment will be used for the same parts, and the detailed explanations thereof will be omitted. FIG. 4 shows an outline of a configuration example of an endoscope system 1 according to the embodiment.

An external memory 132 that is detachably connectable to the video processor 100 is connected to the video processor 100 according to this embodiment. The external memory 132 is a general semiconductor memory or the like. As well as an image memory 130, the external memory 132 stores an endoscope image captured by the user. By using the external memory 132, an endoscope image acquired by a video processor other than the video processor 100 can be used as a sample image.

The video processor 100 of this embodiment comprises a display panel 122 and a touch panel 124 as a display unit instead of the input unit 120 of the first embodiment. The display panel 122 includes, for example, a liquid crystal display element. The display panel 122 displays a screen under the control of a display control unit 160. The touch panel 124 is provided to correspond to the display panel 122. The touch panel 124 detects a position touched by the user and outputs a detection result to a control unit 110.

In this embodiment, a type and a level of structure/outline enhancing are set by using the display panel 122 and the touch panel 124. In a setting mode, a screen as shown in FIG. 5 is first displayed in the display panel 122 in this embodiment. Specifically, a memory selection menu 930 is displayed to allow selection of either an image recorded in the image memory 130 as a sample image or an image recorded in the external memory 132 as a sample image. For example, if the user touches a part indicated as "External memory", the touch panel 124 detects the touch and the detection result is transmitted to the control unit 110.

The external memory 132 stores a plurality of sample images. When "External memory" is selected, a sample image list display screen 940 displays a list of thumbnail images of the images recorded in the external memory 132.

The user selects an image to be used for setting the structure/outline enhancing level or the like from the images by touching the image. The touch panel 124 detects the selection of the user and transmits the detection result to the control unit 110.

When a sample image is selected, the display panel 122 then displays a screen for selecting a type and a level of structure/outline enhancing to set parameters of image processing. The user selects a structure/outline enhancing level or the like by touching the screen. The structure/outline enhancing level or the like is adjusted on the basis of the image displayed on the display panel 122. The other operations are the same as those of the first embodiment.

According to this embodiment, the user can select a sample image for use in setting a structure/outline enhancing level or the like from a number of self-captured sample images.

The display panel 122 independent of the display device 300 is provided, and the screen for setting a structure/outline enhancing level or the like is displayed on the display panel 122. Therefore, for example, an image acquired by the endoscope 200 is displayed in the display device 300, and a structure/outline enhancing level or the like can be set, while the image is maintained without change. In other words, the image displayed in the display device 300 remains unchanged, while only image processing parameters for a sample image displayed on the display panel 122 can be changed, and the sample image whose image quality has been changed can be displayed on the display panel 122. The user selects a setting while variously changing the image quality of the sample image displayed on the display panel 122, and the finally-selected setting can be reflected on the endoscope image acquired by the endoscope 200 and displayed in the display device 300. As described above, according to this embodiment, the structure/outline enhancing level or the like can be changed during observation through, for example, the endoscope 200, without disturbing the observation.

The image displayed on the display panel 122 and used to change the setting is not limited to a sample image captured in the past, but may be an image captured by the endoscope 200 when the structure/outlines enhancing level or the like is to be changed.

The video processor 100 may be configured as follows both in the first embodiment and the second embodiment.

In the setting mode, when determining whether the endoscope 200 is or is not connected to the video processor 100, if it is determined that the endoscope is connected to the video processor, a structure/outline enhancing level or the like may be set by using an image captured by the endoscope 200, and if not, a structure/outline enhancing level or the like may be set by using a sample image recorded in the image memory 130 or the like. Thus, the video processor 100 may be configured so that a sample image is used only when the endoscope 200 is not connected to the video processor 100.

Furthermore, in the setting mode, type information or individual discriminating information of the endoscope 200 connected to the video processor 100 may be acquired, and a sample image captured by the same endoscope 200 may be selected from the sample images recorded in the image memory 130. With this configuration, a structure/outline enhancing level or the like can be set also in consideration of characteristics of the endoscope 200.

It is preferable that sample images be prepared for each of type of surgery and type of diseased site. For example, various pathological lesions may be caused depending on the type of surgery, so it is preferable that sample images be prepared respectively for pathological lesions. It is also preferable that sample images be prepared for each of type of diseased site or tissue, such as an esophagus, a stomach, and a large intestine.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope system for use with a subject body and for use with a user, the endoscope system comprising:
    an endoscope that images an inside of the subject body and acquires an endoscope image;
    an image memory that stores, as a sample image, the endoscope image acquired by the endoscope for setting an image quality; and
    a video processor that performs image processing for the endoscope image and displays the endoscope image, the video processor being programmed to function as:
        an image processing unit that produces a processed image by the image processing for changing an image quality of the sample image in accordance with a selection value selected by the user, when the endoscope is not connected to the video processor;
        a display control unit that causes a display unit to display the processed image; and
        a recording unit that records, as a setting value, a value relating to the selection value determined by the user, wherein:
    the image processing unit performs the image processing of the endoscope image acquired by the endoscope based on the setting value recorded in the recording unit when the endoscope is connected to the video processor.

2. The endoscope system of claim 1, wherein the video processor is further programmed to function as:
    a composing unit that produces a composite screen including the processed image and a setting menu to let the user select the selection values, and
    the display control unit causes the display unit to display the composite screen.

3. The endoscope system of claim 2, wherein
    the display unit includes a display device that is independent of the video processor and a display panel connected to the video processor, and
    the display control unit causes the display panel to display the composite screen and causes the display device to display the endoscope image.

4. The endoscope system of claim 1, wherein an external memory storing the sample image is detachably connectable to the video processor.

5. An endoscope system for use with a subject body and for use with a user, the endoscope system comprising:
    an endoscope configured to image an inside of the subject body and acquire an endoscope image;
    an image memory storing the endoscope image acquired by the endoscope as a sample image for setting an image quality;
    a display; and
    a processor programmed to:
        in response to the endoscope being not connected to the processor, perform image processing of the acquired endoscope image to provide a processed image by changing an image quality of the sample image based on a selection value selected by the user;
        display the processed image on the display;
        record a value relating to the selection value selected by the user as a setting value; and
        in response to the endoscope being connected to the processor, perform the image processing of the acquired endoscope image based on the recorded setting value recorded.

6. The endoscope system of claim 5, wherein the processor is further programmed to:
    provide a composite screen including the processed image and a setting menu configured to let the user select the selection values, and
    the display control unit causes the display unit to display the composite screen.

7. The endoscope system of claim 6, further comprising:
    a display device that is independent of the processor, wherein:
    the processor is connected to a display panel of the display, and
    the processor is further programmed to:
        display the composite screen on the display panel, and
        display the endoscopic image on the display device.

8. The endoscope system of claim 5, wherein an external memory storing the sample image is detachably connectable to the processor.

* * * * *